US012560590B2

(12) United States Patent
Weinstock et al.

(10) Patent No.: US 12,560,590 B2
(45) Date of Patent: Feb. 24, 2026

(54) RAPID ANALYSIS OF LIVE CELLS

(71) Applicants: Massachusetts Institute of Technology, Cambridge, MA (US); Dana-Farber Cancer Institute, Inc., Boston, MA (US)

(72) Inventors: David Weinstock, Jamaica Plain, MA (US); Scott R. Manalis, Portland, OR (US); Robert J. Kimmerling, Cambridge, MA (US); Selim Olcum, Cambridge, MA (US)

(73) Assignees: Massachusetts Institute of Technology, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 556 days.

(21) Appl. No.: 16/739,843

(22) Filed: Jan. 10, 2020

(65) Prior Publication Data

US 2020/0319162 A1 Oct. 8, 2020

Related U.S. Application Data

(60) Provisional application No. 62/795,857, filed on Jan. 23, 2019.

(51) Int. Cl.
*G01N 33/50* (2006.01)

(52) U.S. Cl.
CPC ..... *G01N 33/5011* (2013.01); *G01N 33/5044* (2013.01); *G01N 2800/52* (2013.01)

(58) Field of Classification Search
CPC ...................................................... G01N 15/10
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,320,110 A | 6/1994 | Wang | |
| 6,210,891 B1 | 4/2001 | Nyren et al. | |
| 6,223,128 B1 | 4/2001 | Allex et al. | |
| 6,306,597 B1 | 10/2001 | Macevicz | |
| 6,828,100 B1 | 12/2004 | Ronaghi | |
| 6,833,246 B2 | 12/2004 | Balasubramanian | |
| 6,911,345 B2 | 6/2005 | Quake et al. | |
| 7,232,656 B2 | 6/2007 | Balasubramanian et al. | |
| 7,598,035 B2 | 10/2009 | Macevicz | |
| 7,809,509 B2 | 10/2010 | Milosavljevic | |
| 7,835,871 B2 | 11/2010 | Kain et al. | |
| 7,960,120 B2 | 6/2011 | Rigatti et al. | |
| 8,165,821 B2 | 4/2012 | Zhang | |
| 8,209,130 B1 | 6/2012 | Kennedy et al. | |
| 8,418,535 B2 | 4/2013 | Manalis et al. | |
| 9,132,294 B2 | 9/2015 | Zheng et al. | |
| 11,143,548 B2 | 10/2021 | Cermak et al. | |
| 2003/0149535 A1 | 8/2003 | Sudo et al. | |
| 2005/0048644 A1 | 3/2005 | Hedrick et al. | |
| 2005/0084873 A1 | 4/2005 | Krasnoperov et al. | |
| 2006/0024681 A1 | 2/2006 | Smith et al. | |
| 2006/0292611 A1 | 12/2006 | Berka et al. | |
| 2007/0114362 A1 | 5/2007 | Feng et al. | |
| 2009/0053749 A1 | 2/2009 | Manalis et al. | |
| 2009/0318310 A1 | 12/2009 | Liu et al. | |
| 2010/0298255 A1 | 11/2010 | Ballesteros et al. | |
| 2011/0009278 A1 | 1/2011 | Kain et al. | |
| 2011/0230372 A1 | 9/2011 | Willman et al. | |
| 2011/0257889 A1 | 10/2011 | Klammer et al. | |
| 2013/0268474 A1 | 10/2013 | Nizzari et al. | |
| 2013/0337474 A1 | 12/2013 | Vyas et al. | |
| 2015/0140596 A1 | 5/2015 | Mak et al. | |
| 2015/0322530 A1 | 11/2015 | Orsulic et al. | |
| 2015/0353880 A1* | 12/2015 | Clark ................. G01N 15/1475 |
| | | | 435/305.3 |
| 2016/0266127 A1 | 9/2016 | Kuhn et al. | |
| 2017/0117905 A1 | 4/2017 | Cermak et al. | |
| 2017/0232439 A1 | 8/2017 | Suresh et al. | |
| 2018/0299362 A1 | 10/2018 | Kimmerling et al. | |
| 2019/0011435 A1 | 1/2019 | Cagan et al. | |

(Continued)

FOREIGN PATENT DOCUMENTS

| | | |
|---|---|---|
| WO | WO 2008/043040 A2 | 4/2008 |
| WO | WO 2016/075221 A1 | 5/2016 |

(Continued)

OTHER PUBLICATIONS

Son, Sungmin, et al. "Direct observation of mammalian cell growth and size regulation." Nature methods 9.9 (2012): 910-912. (Year: 2012).*

Stevens, Mark M., et al. "Drug sensitivity of single cancer cells is predicted by changes in mass accumulation rate." Nature biotechnology 34.11 (2016): 1161-1167. (Year: 2016).*

Qiu, Xiaolong, et al. "Microfluidic device for mechanical dissociation of cancer cell aggregates into single cells." Lab on a Chip 15.1 (2015): 339-350. (Year: 2015).*

Burg, Thomas P., et al. "Weighing of biomolecules, single cells and single nanoparticles in fluid." nature 446.7139 (2007): 1066-1069. (Year: 2007).*

Mitra, Abhisek, Lopa Mishra, and Shulin Li. "Technologies for deriving primary tumor cells for use in personalized cancer therapy." Trends in biotechnology 31.6 (2013): 347-354. (Year: 2013).*

International Search Report and Written Opinion mailed Jul. 30, 2020, for PCT/US2020/013064.

International Preliminary Report on Patentability mailed Aug. 5, 2021, for PCT/US2020/013064.

(Continued)

*Primary Examiner* — Robert J Yamasaki
(74) *Attorney, Agent, or Firm* — Wolf, Greenfield & Sacks, P.C.

(57) ABSTRACT

A method of rapid functional analysis of cells is provided. A body fluid sample is introduced into a reservoir of a measurement instrument. A living cell is loaded directly from the body fluid sample into a channel of the measurement instrument in the absence of long-term cell culturing, cell passaging, and application of long-term drug pressure to cells. A functional biomarker of the living cells is measured while the living cell flows through the channel. The functional biomarker measured may be mass accumulation rate (MAR) or mass change. The measurement instrument may be a suspended microchannel resonator (SMR).

16 Claims, 7 Drawing Sheets

(56) References Cited

U.S. PATENT DOCUMENTS

| | | | |
|---|---|---|---|
| 2019/0025308 A1 | 1/2019 | Cummings et al. |
| 2020/0224239 A1 | 7/2020 | Ligon et al. |
| 2020/0224279 A1 | 7/2020 | Weinstock et al. |
| 2020/0225239 A1 | 7/2020 | Weinstock et al. |
| 2022/0011296 A1 | 1/2022 | Ligon et al. |

FOREIGN PATENT DOCUMENTS

| | | | |
|---|---|---|---|
| WO | WO 2016/094330 A2 | 6/2016 |
| WO | WO 2017/083592 A1 | 5/2017 |
| WO | WO 2018/191534 A1 | 10/2018 |
| WO | WO 2019/086476 A1 | 5/2019 |
| WO | WO 2020/102595 A1 | 5/2020 |

OTHER PUBLICATIONS

Ben-Hur et al., Support Vector Clustering. Journal of Machine Learning Research. 2001;2:125-37.

Breiman, Random Forests. Machine Learning. 2001;45:5-32. Epub Oct. 2001.

Bryan et al., Measuring single cell mass, vol. and density with dual suspended microchannel resonators. Lab Chip. Feb. 7, 2014;14(3):569-576. doi: 10.1039/c3lc51022k. Author manuscript provided. 16 pages.

Burg et al., Weighing of biomolecules, single cells and single nanoparticles in fluid. Nature. Apr. 26, 2007;446(7139):1066-9. doi: 10.1038/nature05741.

Byun et al., Characterizing deformability and surface friction of cancer cells. PNAS. May 7, 2013;110(19):7580-5.

Calistri et al., Microfluidic active loading of single cells enables analysis of complex clinical specimens. Nat Commun. Nov. 14, 2018;9(1):4784. doi: 10.1038/s41467-018-07283-x. PMID: 30429479; PMCID: PMC6235965. 7 pages.

Cetin et al., Determining therapeutic susceptibility in multiple myeloma by single-cell mass accumulation. Nature Communications. 2017;8:1613. Epub Nov. 20, 2017. 12 pages.

Chen et al., XGBoost: A Scalable Tree Boosting System. KDD '16: Proceedings of the 22nd ACM SIGKDD International Conference on Knowledge Discovery and Data Mining. Aug. 2016:785-94. Epub Aug. 13, 2016.

Cheung et al., Impedance spectroscopy flow cytometry: on-chip label-free cell differentiation. Cytometry A. Jun. 2005;65(2):124-32. doi: 10.1002/cyto.a.20141.

Cunningham, Tissue disaggregation. Methods Mol Biol. 1999; 115:257-60. doi: 10.1385/1-59259-213-9:257.

Danecek et al., The variant call format and VCFtools. Bioinformatics. Aug. 1, 2011;27(15):2156-8. doi: 10.1093/bioinformatics/btr330. Epub Jun. 7, 2011.

Dochow et al., Tumour cell identification by means of Raman spectroscopy in combination with optical traps and microfluidic environments. Lab Chip. Apr. 21, 2011;11(8):1484-90. doi: 10.1039/c0lc00612b. Epub Feb. 22, 2011.

Dunn et al., Emerging insights into the molecular and cellular basis of glioblastoma. Genes & Development. 2012;26:756-84.

Dunnen et al., Mutation nomenclature. Curr Protoc Hum Genet. Aug. 2003;Chapter 7:Unit 7.13. 8 pages.

Filbin et al., Developmental and oncogenic programs in H3K27M gliomas dissected by single-cell RNA-seq. Science. Apr. 20, 2018;360(6386):331-335. doi: 10.1126/science.aao4750. Author manuscript provided. 11 pages.

Freund et al., A Decision-Theoretic Generalization of On-Line Learning and an Application to Boosting. Journal of Computer and System Sciences. Aug. 1997;55(1):119-39.

Gandara et al., Blood-based tumor mutational burden as a predictor of clinical benefit in non-small-cell lung cancer patients treated with atezolizumab. Nat Med. Sep. 2018;24(9):1441-1448. doi: 10.1038/s41591-018-0134-3. Epub Aug. 6, 2018. Abstract only. 1 page.

George et al., Distinguishing modes of cell death using the ImageStream multispectral imaging flow cytometer. Cytometry A. Jun. 2004;59(2):237-45. doi: 10.1002/cyto.a.20048.

Gossett et al., Hydrodynamic stretching of single cells for large population mechanical phenotyping. PNAS. May 15, 2012;109(20):7630-5.

Grommes et al., Bruton's Tyrosine Kinase (BTK) Inhibitor, Ibrutinib, in Patients With Newly Diagnosed or Refractory/Recurrent Primary Central Nervous System Lymphoma (PCNSL) and Refractory/Recurrent Secondary Central Nervous System Lymphoma (SCNSL). ClinicalTrials.gov. NCT02315326. Last accessed Jan. 20, 2022 as updated Nov. 27, 2017.

Gu et al., Longitudinal Flow Cytometry Identified "Minimal Residual Disease" (MRD) Evolution Patterns for Predicting the Prognosis of Patients with Transplant-Eligible Multiple Myeloma. Biol Blood Marrow Transplant. Dec. 2018;24(12):2568-2574. doi: 10.1016/j.bbmt.2018.07.040. Epub Aug. 22, 2018.

Guck et al., The optical stretcher: a novel laser tool to micromanipulate cells. Biophys J. Aug. 2001;81(2):767-784.

Hellmann et al., Nivolumab plus Ipilimumab in Lung Cancer with a High Tumor Mutational Burden. N Engl J Med. May 31, 2018;378(22):2093-2104. doi: 10.1056/NEJMoa1801946. Epub Apr. 16, 2018.

Lee et al., Suspended microchannel resonators with piezoresistive sensors. Lab on a Chip. 2011;11(4):645-61. Epub Dec. 22, 2010.

Lee, A Study of Abemaciclib in Recurrent Glioblastoma. ClinicalTrials.gov. NCT02981940. Last accessed Jan. 20, 2022 as updated Mar. 26, 2018 from <https://clinicaltrials.gov/ct2/history/NCT02981940?V_10=View#StudyPageTop>.

Li et al., The Sequence Alignment/Map format and SAMtools. Bioinformatics. Aug. 15, 2009;25(16):2078-9. doi: 10.1093/bioinformatics/btp352. Epub Jun. 8, 2009.

Lin et al., Living Single Cell Analysis Platform Utilizing Microchannel, Single Cell Chamber, and Extended-nano Channel. Anal Sci. 2016;32(1):75-8. doi: 10.2116/analsci.32.75. PMID: 26753709.

Luskin et al., Can Minimal Residual Disease Determination in Acute Myeloid Leukemia Be Used in Clinical Practice? J Oncol Pract. Aug. 2017;13(8):471-480. doi: 10.1200/JOP.2017.021675.

Luskin et al., Targeting minimal residual disease: a path to cure? Nat Rev Cancer. Apr. 2018;18(4):255-263. doi: 10.1038/nrc.2017.125. Epub Jan. 29, 2018. Author manuscript provided. 22 pages.

Mason et al., Boosting Algorithms as Gradient Descent. Advances in Neural Information Processing Systems 12: Proceedings of the 1999 Conference. MIT Press. Solla et al., Eds. 2000:512-518.

Mckenna et al., The Genome Analysis Toolkit: a MapReduce framework for analyzing next- generation DNA sequencing data. Genome Res. Sep. 2010;20(9):1297-303. doi: 10.1101/gr.107524. 110. Epub Jul. 19, 2010.

Ning et al., SSAHA: a fast search method for large DNA databases. Genome Res. Oct. 2001;11(10):1725-9. doi: 10.1101/gr.194201.

Otto et al., Real-time deformability cytometry: on-the-fly cell mechanical phenotyping. Nat Methods. Mar. 2015;12(3):199-202, 4 p following 202. doi: 10.1038/nmeth.3281. Epub Feb. 2, 2015.

Press et al., Section 16.5. Support Vector Machines. Numerical Recipes: The Art of Scientific Computing (3rd ed.). New York, NY. Cambridge University. 2007:883-98.

Rajer et al., Quantitative analysis of fine needle aspiration biopsy samples. Radiol Oncol. 2005;39(4):269-72.

Raphael et al., Identifying driver mutations in sequenced cancer genomes: computational approaches to enable precision medicine. Genome Med. Jan. 30, 2014;6(1):5. 17 pages. doi: 10.1186/gm524.

Rosenbluth et al., Analyzing cell mechanics in hematologic diseases with microfluidic biophysical flow cytometry. Lab on a Chip. 2008;8(7): 1062-70. Epub Jun. 5, 2008.

Stevens et al., Drug sensitivity of single cancer cells is predicted by changes in mass accumulation rate. Nature Biotechnology. Nov. 2016;34(11):1161-7. Epub Oct. 10, 2016.

Wang et al., Enhanced cell sorting and manipulation with combined optical tweezer and microfluidic chip technologies. Lab Chip. Nov. 7, 2011;11(21):3656-62. doi: 10.1039/c11c20653b. Epub Sep. 14, 2011.

Warren et al. Assembling millions of short DNA sequences using SSAKE. Bioinformatics. Feb. 15, 2007;23(4):500-1.

(56) References Cited

OTHER PUBLICATIONS

Invitation to Pay Additional Fees mailed Apr. 28, 2020 for Application No. PCT/US2020/013064.

Cermak et al., High-throughput measurement of single-cell growth rates using serial microfluidic mass sensor arrays. Nat Biotechnol. Oct. 2016;34(10):1052-9. Author manuscript provided. Published Mar. 5, 2017. 37 pages.

[No Author Listed], Using cancer cells mass to predict treatment response. Technology Networks. Nov. 24, 2016. <https://https://www.technologynetworks.com/cell-science/news/using-cancer-cells-mass-to-predict-treatment-response-213178>. 3 pages.

Cobb et al., Sepsis gene expression profiling: murine splenic compared with hepatic responses determined by using complementary DNA microarrays. Crit Care Med. Dec. 2002;30(12):2711-21.

Enard et al., Intra- and interspecific variation in primate gene expression patterns. Science. Apr. 12, 2002;296(5566):340-3.

Fenizia et al., Measuring tumor mutation burden in non-small cell lung cancer: tissue versus liquid biopsy. Transl Lung Cancer Res. Dec. 2018;7(6):668-677.

Heeke et al., Tumor mutational burden assessment as a predictive biomarker for immunotherapy in lung cancer patients: getting ready for prime-time or not? Transl Lung Cancer Res. Dec. 2018;7(6):631-638.

Kimmerling et al., Linking single-cell measurements of mass, growth rate, and gene expression. Genome Biol. Nov. 27, 2018;19(1):207.

Murakami et al., Linking biophysical and transcriptional profiles of in vivo-treated human leukemias on a single-cell level uniquely resolves subpopulations of response. Blood. Dec. 8, 2017; 130(1):3987.

Nebot-Bral et al., Why is immunotherapy effective (or not) in patients with MSI/MMRD tumors? Bull Cancer. Feb. 2019;106(2):105-113. doi: 10.1016/j.bulcan.2018.08.007. Epub Oct. 17, 2018.

[No Author Listed], "Effusion" definition and meaning. Merriam-Webster Dictionary. Retrieved from <https://www.merriam-webster.com/dictionary/effusion> on Oct. 7, 2023. 1 page.

[No Author Listed], What is a cell? Definition, structure, types and functions. Retrieved from <https://byjus.com/biology/cells/#:~:text=Cells] on Oct. 10, 2023. 11 pages.

* cited by examiner

110   Obtain sample

120   Introduce sample

130   Measure functional biomarker

140   Analyze

150   Report

610 ～ Obtain sample

620 ～ Introduce sample

630 ～ Dose sample

640 ～ Measure functional biomarker

650 ～ Analyze

660 ～ Report

RAPID ANALYSIS OF LIVE CELLS

RELATED APPLICATION

This application claims priority under 35 U.S.C. § 119(e) to U.S. Provisional Application Ser. No. 62/795,857, filed Jan. 23, 2019, the entire contents of which are incorporated by reference herein.

GOVERNMENT SPONSORSHIP

This invention was made with government support under CA170592, CA191143, and CA217377 awarded by the National Institutes of Health. The government has certain rights in the invention.

TECHNICAL FIELD

The invention relates to analysis of living cells for precision medicine.

BACKGROUND

Cancer continues to be a leading cause of death. While scientists continue to develop new drugs for treatment, it is often difficult to determine whether a treatment will be effective for a particular patient. The emerging field of precision medicine offers the promise of individualized disease diagnosis and monitoring, as well as tools for therapeutic selection that are narrowly tailored to an individual disease or narrowly-defined disease category.

Precision medicine refers to the tailoring of medical treatment to individual patients and the classification of individuals into subpopulations based on shared treatment response. In precision medicine, patient-specific genomic markers drive therapeutic selection, thus maximizing the impact of therapy for each patient.

Next-generation sequencing (NGS) technologies make up the core of traditional precision medicine approaches. Clinicians use NGS to screen for cancer-associated mutations or variations in gene expression. The reliance on genomics in precision medicine places limits on the dynamic range of diagnostic assays and potential treatment options.

SUMMARY

The invention provides methods and devices for rapidly measuring functional properties of living cells. Isolated living cells are obtained from tissue by a sample procedure such as fine needle aspiration. The cells are measured with minimal processing and no requirement of overnight culturing. Methods of the invention measure functional properties of living cells, including properties indicative of cellular growth or health. The measurements are rapid and may be performed in a few hours of sample collection. The measurements require as few as ten minutes of instrument run time and have an error rate of about 0.01%. Upon measurement completion, individual cells are still viable and can be subjected to further measurements. For example, subsequent measurement shows mass change over time. In addition, the same cells can be subjected to genomic analysis. Methods and devices of the invention add a new modality of measurement that is complementary to genomic analysis. Living cells from patient samples are flowed directly into an instrument, such as a suspended microchannel resonator. Functional properties, such as cellular mass change reveals, for example, if the cells are growing, stationary, or atrophying. A change in cellular mass is indicative of health status and/or therapeutic response. Rapid and precise measurements of cellular mass according to the invention provide impactful diagnostic information. Because the invention uses live cells, traditional NGS approaches can be combined with methods of the invention to provide and additional layer of diagnostic impact.

Methods and devices of the invention are useful to identify cancer or pre-cancer cells in a tissue sample such as a fine needle aspirate. The invention is further useful for ex vivo testing of drug response. Moreover, after treatment, methods and devices of the invention may be used to monitor recurrence, remission, or relapse.

Methods and devices of the disclosure are useful to measure growth rate even when only a small number of cells is available. Thus, there are no requirements to obtain a sample of specific size or to culture the sample prior to measurement. Moreover, a sample can be applied directly to a measurement device of the invention without significant sample preparation. In a preferred embodiment, cells are measured in a microfluidic channel. Sample may be applied directly to the channel and cells are separated as they flow through the channel, thereby allowing for measurement of individual cells. For example, a preferred sample comprises as few as about 500 for effective measurement. A small amount of cells may be used due to the precision of the methods of measurement of the present invention. Therefore, methods of the invention are useful when limited amount of sample is available for testing.

In addition, methods of the invention are amenable to multiplex analysis. For example, a tissue sample comprising only a few thousand cells can yield information on as many as 20 different conditions. Such a small sample does not have enough cells for traditional measurement methods (e.g., optical detection).

The invention provides methods and instruments for the measurement of mass (or mass accumulation) or other functional measurements to assess the disease status of the cell. According to methods of the invention, mass accumulation is measured in about two to about four hours, and most preferably about two hours or less. Moreover, methods of the invention are significantly more precise than traditional measurement methods. For example, the present invention is about 10 to about 100 times more precise than measurements obtained using optical measurement techniques.

While the presence of culture medium affects traditional measurement techniques (e.g., optical techniques), culture medium does not impact measurement according to the invention. In the invention, mass measurement is accomplished using no or substantially no culture medium. This allows methods of the invention to be carried out more rapidly than other measurement methods. For example, sample preparation according to the invention is about 20 minutes, and mass is measured in about two to about four hours. In addition, many other measurement methods, such as optical methods, typically have 10% error. In contrast, the present invention has less than about 1% error, and in some instances has about 0.5% error.

Methods of the invention provide a rapid measure of growth rates of living individual cells in comparison to other functional biomarker measurement methods. For example, a sample preparation is accomplished in less than about one hour. Further, cells may optionally be dosed with a test therapeutic compound in about three hours to about five hours. In a preferred embodiment, functional measurement requires from about two hours to about four hours. The rapid analysis of the present invention is possible because the sample can be obtained from a subject, suspended in media, and introduced to the measurement instrument without extra added steps, such as incubation of the cells.

In certain aspects, the disclosure provides a method of rapid functional analysis of cells. Methods include obtaining, by fine needle aspiration, a sample comprising at least one live cell. Methods according to the invention proceed without incubating the sample to culture cells. The cell is introduced to an input reservoir of a measurement instrument. The functional biomarker of the cell is measured while the cell flows through a channel of the instrument. In preferred embodiments, the functional biomarker is mass or mass accumulation rate (MAR). Preferably, the error rate of MAR measurement is about 0.01%. In preferred embodiments, the measurement instrument performs the measurement step using a suspended microchannel resonator (SMR), or an array thereof. In an embodiment, the channel passes through an array of SMRs, and each successive pair of SMRs is separated by a portion of the channel that provides a delay.

In preferred embodiments, the sample is drawn from a solid tumor by fine needle aspiration. The sample comprises a tissue sample or clump of cells having the cell therein. In an embodiment, the sample may include fewer than about 500 cells. The sample is disaggregated to release the cell, such as by exposing the sample to one or more proteases. The cell is washed from the sample in a nutrient medium. The nutrient medium, including the cell, is delivered to the input reservoir in the introducing step. After measurement, the cell leaves the channel in a living state and is available for subsequent analysis. In an embodiment, methods according the invention are used to make measurements of cancer or immune cells. Preferably, a functional measurement of living cancer cells is provided as a measure of cancer.

In certain aspects, the invention is directed to methods of rapid functional analysis of cells. A sample is introduced into a reservoir of a measurement instrument. A live cell is loaded directly from the sample into a channel of the instrument. Steps of the invention proceed in the absence of long-term cell culturing, cell passaging, and application of long-term drug pressure to cells. A functional biomarker of the cell is measured while the cell flows through the channel.

In an embodiment, the measurement instrument is used for sample preparation, dosing, and functional measurement and comprises a sample preparation component, a dosing component, and a functional measurement component. In an example, the functional measurement component comprises a suspended microchannel resonator (SMR). The channel passes through an array of SMRs, and each successive pair of SMRs is separated by a portion of the channel that provides a delay.

An example of a functional biomarker is mass accumulation rate (MAR) or a change in mass. Using methods of the invention, the MAR or mass change is measured with an error rate of about 0.01%. The MAR or mass change is measured in about 20 minutes to about 2 hours.

The sample is obtained by any suitable means. Examples of obtaining the sample include needle aspiration. Notably, the sample does not comprise fixed cells. Incubation of the sample is not required. Thus, methods of the invention require less time for sample preparation and functional biomarker measurement than traditional measurement methods. For example, the measuring step is performed within less than about 3 hours of cells being isolated from the sample. The measuring step is performed within less than about 48 hours of the sample having been drawn from a subject. In some instances, the measuring step is performed within less than about 36 hours of drawing the sample from a subject. The measuring step requires less than about 30 minutes of time with the living cell in the channel.

Notably, methods of the invention analyze the sample without destroying the cells. Therefore, the invention provides methods of non-destructive testing. In the invention, the cell is isolated and measurement does not harm the cell. The method is done so quickly that the duration of measurement is within the natural state of the cell. This allows further testing of the sample after measurement of the functional biomarker. In an example, cells are extracted from a subject. A mass accumulation rate of the cell is measured while the cell flows through a measurement instrument (e.g. a suspended microchannel resonator). Cells collected after flowing through the microchannel(s) in the SMR are not destroyed and are available for further analysis. In an example, the cells are further analyzed using flow cytometry. The reverse process is not possible because the flow cytometry process destroys the cells. Therefore, analysis of the cells using flow cytometry followed by functional biomarker analysis using methods of the invention is not possible.

The cells in the sample are any biological cells. In some examples, the cells are cancer cells. The method provides a functional measurement of living cancer cells as a measure of cancer. Embodiments of the method are used for screening drugs. In an example, the cancer cells are dosed with a cancer treatment drug, measured using methods of the invention, and analyzed. The analysis results reported include an indication of whether the dose applied to the cancer cells affected the MAR. In some instances, the cells are immune cells and methods of the invention provide a functional measurement of living immune cells as a measure of cancer. Such methods are used for screening drugs.

Aspects of the invention provide devices and methods for in vitro functional measurement on living cells obtained by fine needle aspiration. Measurements made on living cells reveal not only the presence of cancer cells, but also elucidate the functional aspects of those cells over time, including their response to prospective therapeutic intervention. Measurements made on living cells according to the invention provide a real-time, dynamic view of the cells, enabling more accurate diagnosis and more effective therapeutic selection.

Measurements according to the invention typically are made on cells obtained by fine needle aspiration to obtain cell clumps, aka tissue samples. Tissue samples may be mechanically or enzymatically dis-aggregated to release individual living cells into a fluidic measurement platform. Functional measurements are then made on the living cells. In fact, after measuring a property of a cell, the cell remains alive and is available for subsequent analyses.

Instruments of the disclosure are used to measure cellular functions characteristic of cancer cells in fine needle aspirates. The instruments are used to measure the growth of the cells by measuring mass or change in mass in the cells. Healthy, differentiated somatic cells from a tissue sample are expected to exhibit stable mass. When live cells from a fine needle aspirate are measured with instruments of the disclosure, the detection of mass accumulation, or growth, indicates the presence of cancerous or pre-cancerous cells in the tissue. Moreover, known cancer cells that are responding favorably to a therapeutic may exhibit loss of mass. Instruments of the disclosure make sensitive and precise measurements of mass or change in mass indicative of cancer through the use of a suspended microchannel resonator. The instruments use a structure such as a cantilever that contains a fluidic microchannel. Living cells are flowed through the structure, which is resonated and its frequency of resonation is measured. The frequency at which a structure resonates is dependent on its mass and by measuring the frequency of at which the cantilever resonates, the instrument can compute a mass, or change in mass, of a living cell in the fluidic microchannel. By flowing the isolated living cells from the tissue sample through such devices, one observes the function of those cells, such as whether they are growing and accumulating mass or not. The mass accumulation or rate of mass accumulation can be related to clinically important property such as the presence of cancer cells or the efficacy of a therapeutic on cancer cells.

In certain aspects, the invention provides a method for assessing a cancer biomarker. Such methods include obtaining a tissue sample comprising living cells (e.g., preferably by fine needle aspiration), disaggregating the tissue sample and loading individual live cells into an input channel of a measurement instrument, and flowing the live cells through the measurement instrument to measure a functional property of the live cells. The tissue sample may be obtained from a human subject and the living cells may include cancer cells or immune cells. The functional property may be mass or mass accumulation rate (MAR). Preferably the mass is measured with a precision of at least about 0.01% of cell mass. The MAR may be measured with a precision of at least about 0.1% per hour. A duration of measuring the MAR is from about 20 minutes to about 3 hours. The functional property may be measured from the live cells within less than about three hours of the tissue sample being obtained by biopsy. The functional property may be measured from the live cells within less than about 3 hours after the disaggregating step.

In certain embodiments, the measurement instrument comprises a suspended microchannel resonator (SMR). In some embodiments, the live cells are measured and leave the instrument in a living state, accessible for a subsequent assay. For example, the method may include performing the assay on at least one cell from the living cells. The assay may be for example genome sequencing.

In certain preferred embodiments, the living cells are cancer cells. The tissue sample may be obtained from a solid tumor (such as a tumor of the bone, bladder, brain, breast, colon, esophagus, gastrointestinal tract, urinary tract, kidney, liver, lung, nervous system, ovary, pancreas, prostate, retina, skin, stomach, testicles, or uterus of a subject). The tissue sample may be provided via, for example, a fine needle aspirate, from a pleural effusion in a subject, or obtained from ascetic fluid in a subject. Masses or clumps of the tissue sample may be disaggregated to release individual cells into media such as culture or maintenance media. Disaggregating the cells may include physical, mechanical, chemical, or proteolytic disaggregation or a combination thereof. Thus in a preferred embodiment, a solid tumor is interrogated via fine needle aspiration to retrieve a cell mass, or tissue sample, that includes cancer cells. The cell mass may be deposited, e.g., on a nitrocellulose membrane and disaggregated using, e.g., proteases such as collagenase and/or displace. Live cells may be washed into a fluidic tube or system with and supported by a suitable media such as a Ham's nutrient mixture. The live cells may be flowed into a loading chamber of a measurement instrument such as a mass-measuring instrument that uses an SMR. A fluidic system of the instrument flows media through the SMR and controls pressure such that isolated individual living cancer cells flow through the SMR. Flow time through the SMR can be less than about 20 minutes to make a measurement of mass or mass accumulation rate and the measurement may be made within about 3 hours of obtaining the sample from the patient by FNA. A cell's mass or mass accumulation rate is measured in the SMR and the cell leaves the SMR alive and intact. The living cell can be passed through other SMRs or back through the same one. That living cell can also be sequestered in a collection tube and/or passed to another instrument for a downstream analysis such as nucleic acid capture and sequencing.

The method includes disaggregating the tissue sample and loading individual live cells into an input channel of a measurement instrument. Any suitable technique may be used for disaggregating the cells. For example, disaggregation may be mechanical, chemical, or enzymatic. A tissue sample or clump of cells may be digested with one more proteases to digest extracellular matrix among the cells, and the sample or clump may be washed with a maintenance or nutrient medium to load isolated individual living cells into a fluidic system such as a channel in a microfluidic device.

DETAILED DESCRIPTION

Figure 1:
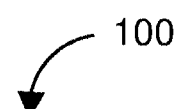
FIG. 1 diagrams a method for the rapid functional analysis of cells.
Figure 1:
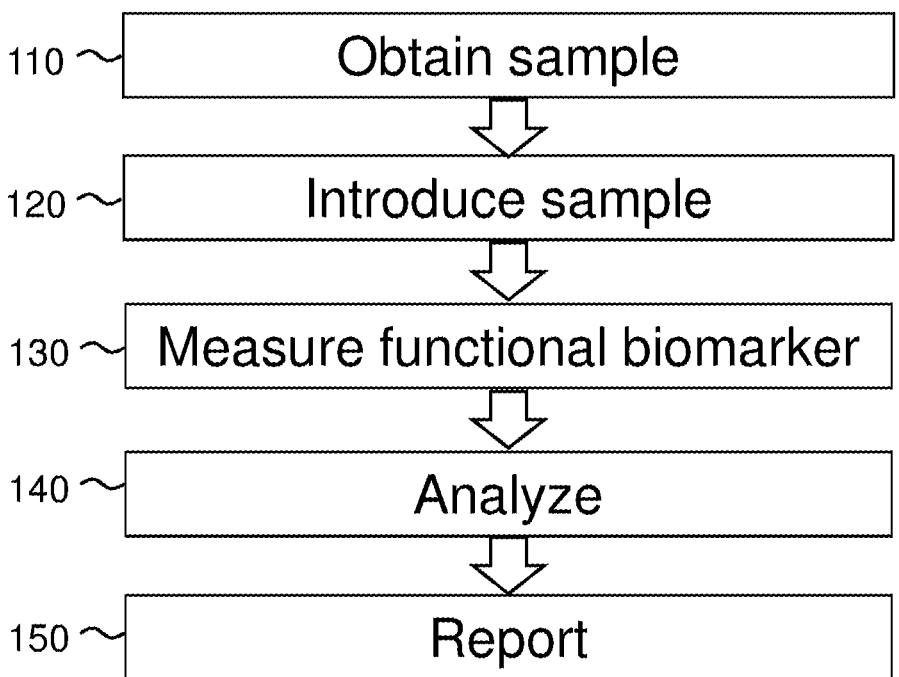

The invention provides devices and methods for functional measurement of living cells. When the cells are obtained from a person suspected of having cancer, measurements can show that cancer cells are present. Measurements over time can show progression of the cancer or how the cancer is reacting to stimulus such as a therapeutic treatment. Measurements according to the invention are made rapidly from samples (e.g., blood draws or fine needle aspirates) and do not require a culturing step to grow the cells. Instruments of the disclosure (e.g., suspended microchannel resonators) are used to measure cellular functions embodying viability of the cells. In an example, instruments are used to measure growth of the cells directly from a sample by measuring mass or change in mass in the cells. The cells are loaded directly into the instrument from a blood or tissue sample without an intervening period for culturing and growth. Those cells drawn from a patient are loaded directly onto the instrument. Functional measurements are obtained within less than about a few hours after the sample is drawn from the patient.

Devices according to the invention make sensitive and precise measurements of mass or change in mass through the use of a suspended microchannel resonator (SMR). The SMR includes a structure such as a cantilever that contains a fluidic microchannel. Living cells are flowed through the structure, which is resonated and its frequency of resonation is measured. The frequency at which a structure resonates is dependent on its mass. By measuring the frequency of at which the cantilever resonates, the instrument computes a mass, or change in mass, of a cell in the fluidic microchannel. By flowing individual cells from the tissue sample through such devices, functions of the cells are observed, such as whether or not the cells are growing and accumulating mass. The mass accumulation or rate of mass accumulation is a clinically important property and is used to indicate the presence of cancer cells or the efficacy of a therapeutic on cancer cells.

Methods according to the invention provide rapid and precise measurement of functional properties of cells without a culturing step. Same-day turnaround is possible, including measuring cell growth while a patient is in a clinic to have a sample taken. Significantly, the measurements may be made from a tissue sample and the measured cells may be living cancer cells from a solid tumor. Thus, the measured functional properties provide a valuable marker of cancer activity. Once the measurements are made, the living cells are available for further analysis, such as genome sequencing or other measurements. Therefore, the invention provides for the functional analysis of cancer cells.

Methods and devices of the disclosure use mass measurement technology for use in precision medicine and oncology. Embodiments of the technology use microchannel resonators to precisely measure mass and mass changes in individual living cells. When used with cancer cells, the changes provide a functional, universal biomarker. The biomarker is available for use by oncologists to monitor the progression of a cancer and to determine how cancer cells respond to therapies. The resonators may be provided within a measurement instrument such as a bench-top instrument into which cells and samples are loaded. For cancers, various techniques may be used to load isolated living cells into a fluidic environment that makes a cell available to the microchannel resonator device. In an example, the invention is used to study living cells from solid tumors, wherein samples may be provided by biopsy or fine needle aspiration.

FIG. 1 diagrams a method 100 for the rapid functional analysis of cells. The method 100 includes obtaining 110 the sample from a subject. The sample is obtained by any suitable means. Examples of obtaining 110 the sample include by needle aspiration, blood draw, liquid biopsy, and bone marrow biopsy. Notably, the sample preferably does not comprise fixed cells (e.g., is not a FFPE tissue slice). Incubation or culturing of the sample is not required by the invention. Further, the invention only requires a small sample size compared to sample sizes necessary in traditional measurement methods (e.g., optical measurement methods). For example, in the invention, the sample comprises about 500 or fewer cells. Methods of the invention are used when limited tissue samples are available for testing and measurement. For example, a tissue sample may comprise about 10,000 cells. Moreover, much smaller sample sizes are tested using methods of the present invention. For example, methods of the invention use a sample having about 500 cells to measure mass accumulation rate (MAR). In some instances, a sample size of 5,000 cells is used to achieve about 2% to about 4% efficiency. If a sample of about 10,000 cells is provided, methods of the invention may be used to test about 20 different conditions. For example, if 500 cells are dosed with a first drug to determine the effects of the drug on mass accumulation rate of the cells, as many as 20 different drugs may be tested with a sample containing 10,000 cells.

The method 100 comprises introducing 120 the sample to a measurement instrument. For example, a body fluid sample is introduced 120 into a reservoir of a measurement instrument and a living cell is loaded directly from the body fluid sample into a channel of the measurement instrument in the absence of long-term cell culturing, cell passaging, and application of long-term drug pressure to cells. The method 100 further comprises measuring 130 a functional biomarker. For example, the functional biomarker of the living cell is measured while it flows through the channel. An example of a functional biomarker is mass accumulation rate (MAR) or a change in mass. Using methods of the invention, the MAR or mass change is measured with a precision or error rate of about 0.01%. The MAR or mass change is measured in about 20 minutes to about 2 hours.

In the method 100, living cells are analyzed 140 based on measurements made 130 using an instrument of the disclosure. The instrument is used to measure mass or accumulation of mass while a cell travels through microchannels in the instrument. Mass accumulation is measured in less than about two hours. Precision of the invention in determining the mass of individual cells is much more precise than traditional measurement methods. For example, measurements using methods according to the invention are about 10 to about 100 times more precise than measurements obtained using optical measuring techniques. The rate of mass change of a single cell is measured over about two to about four hours. The method 100 includes producing 150 a report that provides information about a patient or sample. The measurement is made 130 rapidly without the requirement of a separate culturing or enrichment step.

Due to the lack of a culturing step, methods of the invention are carried out more rapidly than traditional measurement methods. For example, sample preparation of the invention is about 20 minutes, and a measurement of a change in mass in the invention is obtained in about two to about three hours. In traditional measurement methods where culture media is present, the duration of measurement extends much longer. This is because traditional methods include steps of finding the cells and measuring the reading of the cells, which may be obscured due to the culture medium. The invention provides a faster, more precise method of measuring a functional biomarker of a single living cell, such as mass accumulation rate. Many traditional measurement methods, such as optical measurement methods, typically have 10% error. In contrast, the invention has less than about 1% error, and in some instances has about 0.5% error.

Methods of the invention provide a rapid measure of growth rates of living individual cells in comparison to other functional biomarker measurement methods. For example, sample preparation of the present invention is less than about one hour. Further, dosing the sample with a therapeutic treatment or drug is about three hours to about five hours. Obtaining the functional measurement is about two hours. Rapid analysis of the invention is possible because the sample can be obtained from a subject, suspended in media, and introduced to the measurement without extra added steps, such as incubation of the cells.

Because incubation is not a required step, methods of the invention require less time than other measurement methods for sample preparation and functional biomarker measurement. For example, the measuring step is performed within less than about three hours of isolating cells from a body fluid sample. The measuring step is performed within less than about 48 hours of drawing the body fluid sample from a subject. In some instances, the measuring step is performed within less than about 36 hours of drawing the body fluid sample from the subject. The measuring step requires less than about 30 minutes with the cell flowing in the channel.

Notably, methods of the invention analyze the sample without destroying the cells. This allows further testing of the sample after the functional biomarker has been measured using the invention. Living cells are extracted from a subject. The cells are flowed through a measurement instrument such as a suspended microchannel resonator to measure a mass accumulation rate of the cells. The cells are collected after flowing through the microchannel(s) in the SMR. Those cells are not destroyed and are available for further testing. In an example, the cells are tested using flow cytometry. Importantly, the reverse process is not possible—conducting flow cytometry analysis of the cells followed by measurement of functional biomarkers using the invention—because the cells are destroyed by the flow cytometry process.

The cells in the sample may be any biological cells. In some examples, the cells are cancer cells, and the method provides a functional measurement of living cancer cells as a measure of cancer. In some embodiments, the method is used for screening drugs. For example, the cancer cells may be dosed with a cancer treatment therapeutic or drug, measured using methods of the invention, and analyzed. The analysis results reported include an indication of whether the dose applied to the cancer cells affected the MAR. In some instances, the cells are immune cells and methods of the invention provide a functional measurement of living immune cells as a measure of cancer. Such a method may be used for screening drugs.

The method 100 may further comprise analysis 140 and reporting 150. The method 100 further includes analyzing data 140 from the measurement step. For example, the analysis may specify the mass accumulation rate of the cell and the mass change. The method 100 further includes providing a report 150. The report may comprise information related to the analysis and measurement. For example, the report may provide the analysis results.

Obtaining functional analysis measurements using the present invention is possible with only minimal use of culture medium. Long-term cell culturing, passaging, or applying long term drug pressure is not required. Instead, the invention uses cell culture medium only for the duration of the analysis. Estimated preparation time from the start of sample delivery is less than about one hour, dosing of the sample with a drug or therapeutic treatment is about three hours to about five hours, and measurement of the functional biomarker is about two hours.

In certain embodiments, the measurement instrument includes the sample preparation, dosing, and functional measurement components in a single instrument. In other embodiments, the sample preparation, dosing, and functional measurement components are performed in different measurement instruments.

The sample may be obtained by any suitable means. Examples of obtaining the sample include fine needle aspiration, blood draw, and bone marrow biopsy. Notably, the sample does not need to be in liquid form. For instance, in fine needle aspiration and bone marrow biopsy, a solid biological sample is obtained from a subject. In an example, the solid biological sample is then suspended in a media and introduced to the measurement instrument. Non-limiting examples of media include saline, nutrient broth, and agar medium.

Figure 2:
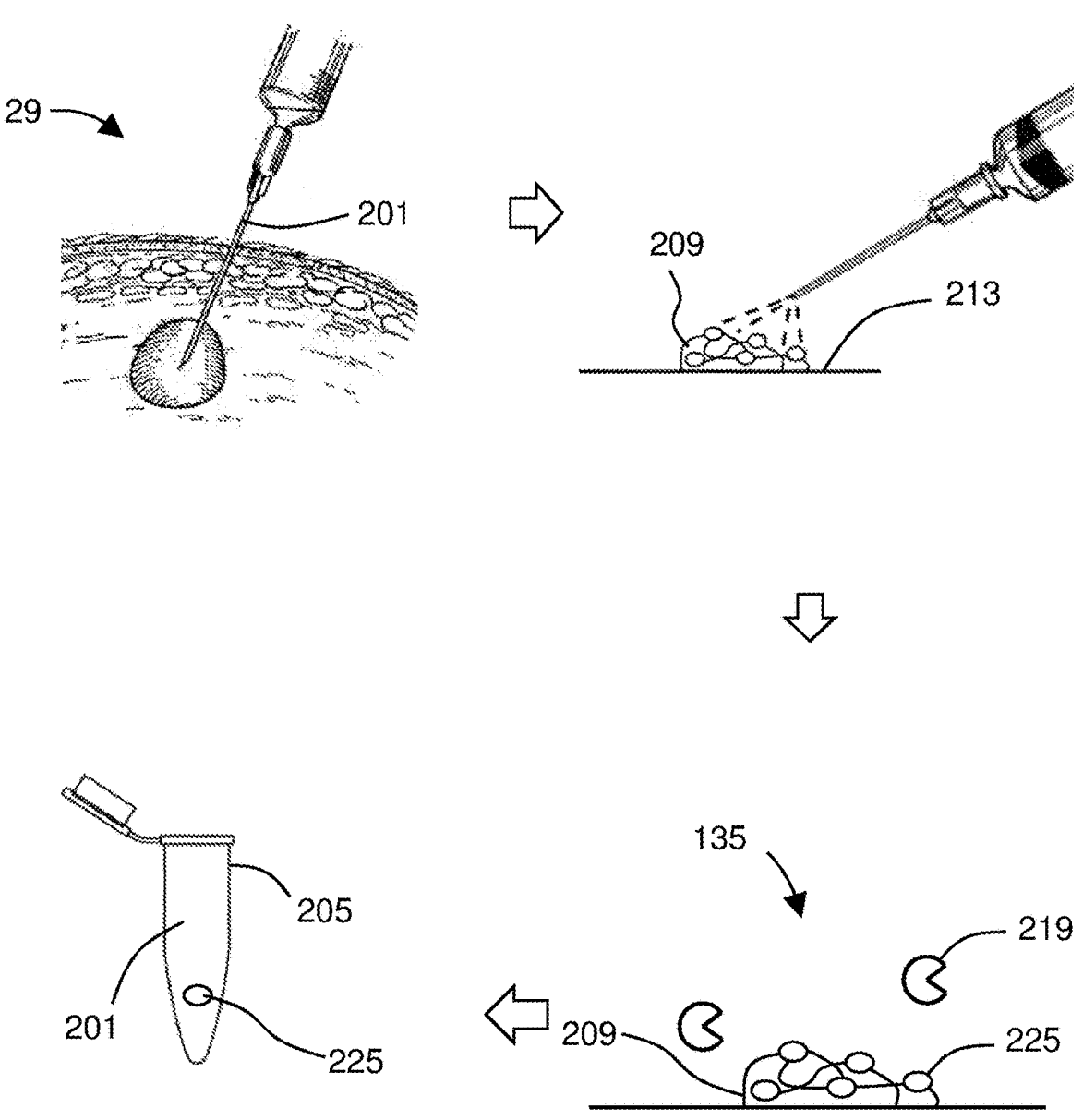
FIG. 2 shows obtaining a sample that includes at least one living cell.

FIG. 2 shows obtaining 129 a sample 201. The sample 201 includes one or more live cells such as a cancer cell or an immune cell. Samples may be collected and stored in their own container 205, such as a tube or flask such as the 1.5 mL micro-centrifuge tube sold under the trademark EPPENDORF FLEX-TUBES by Eppendorf, Inc. (Enfield, CT). The one or more live cells are isolated from a biological sample of a patient known to have, or suspected of having, cancer. A biological sample may include a human tissue or bodily fluid and may be collected in any clinically acceptable manner. For example, the sample may include a fine needle aspirate or a biopsy from a tissue known to be, or suspected of being, cancerous. The sample may include a bodily fluid from a patient either known to include, or suspected of including, cancer cells or cancer-related cells (i.e., immune cells).

In some embodiments, the sample is from a patient having or suspected of having a cancer. The cancer may be a leukemia, a lymphoma, or a myeloma. The cancer may be a melanoma, a carcinoma, or a sarcoma. In certain embodiments, the cancer involves a solid tumor of, for example, the esophagus, kidneys, uterus, ovaries, thyroid, breast, liver, gallbladder, stomach, pancreas, or colon. A sample may be obtained 129 by a biopsy procedure.

In certain preferred embodiments, the tissue sample is obtained from a solid tumor and the tumor is from one selected from the group consisting of a bone, bladder, brain, breast, colon, esophagus, gastrointestinal tract, urinary tract, kidney, liver, lung, nervous system, ovary, pancreas, prostate, retina, skin, stomach, testicles, and uterus of a subject. Fine needle aspiration may be used to obtain 129 the sample from a tumor. As shown, a solid tumor is interrogated via fine needle aspiration to retrieve a cell mass, or tissue sample, that includes cancer cells. Methods may include using a needle 201, preferably fine-needle aspiration biopsy using a sharp 25-gauge, 1-inch long needle. One or more separate aspirates may be made from different areas of the tumor. A suitable needle 201 is the sharp 25-gauge, 1-inch long needle sold under the trademark PRECISION GLUIDE by BD (Franklin Lakes, NJ). The needle may be attached via flexible plastic tubing to a 10 ml aspirating syringe. The procedure may be monitored under indirect ophthalmoscopy.

The biopsy needle may be passed into a lesion or tumor. Once the tip of the needle is advanced into the lesion, the tumor cells are aspirated. The plunger of the syringe may be forcibly pulled and quickly released a few times, allowing the suction force in the line to equilibrate. The needle is withdrawn and a tissue sample or clump of cells is deposited in or on a substrate 213. Any suitable substrate 213 may be used such as a slide, culture dish, membrane, or other material. In some embodiments, the clump of cells 209 is deposited on a surface within a collection tube or flask, such as a 1.5 mL microcentrifuge tube sold under the trademark EPPENDORF. Each aspirate may be flushed into the flask using culture media, saline, or a maintenance/nutrient media. The aspiration material may be filtered to deposit clumps or samples of tissue on the surface of a filter membrane. The cell mass may be deposited, e.g., on a nitrocellulose membrane and disaggregated using, e.g., proteases such as collagenase and/or displace. Live cells may be washed into a fluidic tube or system with and supported by a suitable media such as a Ham's nutrient mixture. For information, see Rajer, 2005, Quantitative analysis of fine needle aspiration biopsy samples, Radiol Oncol 39(4):269-72, incorporated by reference.

The tissue sample or clump of cells 209 is disaggregated 135. Any suitable technique may be used to disaggregate 135 the tissue sample/clump of cells 209. For example, disaggregation may include physical or mechanical disaggregation, chemical disaggregation, proteolytic disaggregation, or any combination thereof. In some embodiments, proteolytic disaggregation is performed using one or more enzymes 219. Any suitable enzymes may be used. In some embodiments, the tissue sample/clump of cells 209 is washed with and digested by collagenase I and dispase II. The resultant free cells may be held in a suitable nutrient media such as, for example, Ham's F12 Kaighn's Modification medium in presence of 1 mU/mL bovine thyrotropin (TSH), 10 µg/mL human insulin, 6 µg/mL transferrin, and 10-8 M hydrocortisone.

Thus the method 101 may include obtaining a fine needle aspirate tissue sample that includes live cancer cells that have been disaggregated from any tissue or clump so that individual live cells may be separately addressed, e.g., subjected to a measurement of some functional property of those cells. Other methods may be used for obtaining a sample 201 and isolating at least one living cell 225.

In a preferred embodiment, the obtaining step 110 includes drawing the sample from a solid tumor by fine needles aspiration. For example, a cell mass is retrieved from a solid tumor via fine needle aspiration, or tissue sample, that includes cancer cells. Methods include using a needle, such as a fine-needle aspiration biopsy using a sharp 25-gauge, 1-inch long needle. A suitable needle is the sharp 25-gauge, 1-inch long needle sold under the trademark PRECISION GLUIDE by BD (Franklin Lakes, NJ). The needle may be attached to a 10 ml aspirating syringe.

The biopsy needle may be passed into a lesion or tumor. Once the tip of the needle is advanced into the lesion, the tumor cells are aspirated. The plunger of the syringe may be pulled and released a few times, allowing the suction force to equilibrate. The needle is withdrawn and a tissue sample or clump of cells is deposited in or on a substrate such as a slide, culture dish, membrane, or other material. In some embodiments, the clump of cells is deposited on a surface within a collection tube or flask, such as a 1.5 mL microcentrifuge tube sold under the trademark EPPENDORF. Each aspirate may be flushed into the flask using culture media, saline, or a maintenance/nutrient media. The aspiration material may be filtered to deposit clumps or samples of tissue on the surface of a filter membrane. The cell mass may be deposited, e.g., on a nitrocellulose membrane and disaggregated using, e.g., proteases such as collagenase and/or dispase. Live cells may be washed into a fluidic tube or system with and supported by a suitable media such as a Ham's nutrient mixture. For information, see Rajer, 2005, Quantitative analysis of fine needle aspiration biopsy samples, Radiol Oncol 39(4):269-72, incorporated by reference.

The tissue sample or clump of cells is disaggregated. Any suitable technique may be used to disaggregate the tissue sample/clump of cells. For example, disaggregation may include physical or mechanical disaggregation, chemical disaggregation, proteolytic disaggregation, or any combination thereof. In some embodiments, proteolytic disaggregation is performed using one or more enzymes. Any suitable enzyme is used. In some embodiments, the tissue sample/clump of cells is washed with and digested by collagenase I and dispase II. The resultant free cells may be held in a suitable nutrient media such as, for example, Ham's F12 Kaighn's Modification medium in presence of 1 mU/mL bovine thyrotropin (TSH), 10 µg/mL human insulin, 6 µg/mL transferrin, and 10-8 M hydrocortisone.

The method 100 includes obtaining 110 a fine needle aspirate tissue sample that includes live cancer cells disaggregated from any tissue or clump. The individual live cells are separately addressed, e.g., subjected to a measurement of a functional property of those cells.

Figure 3:
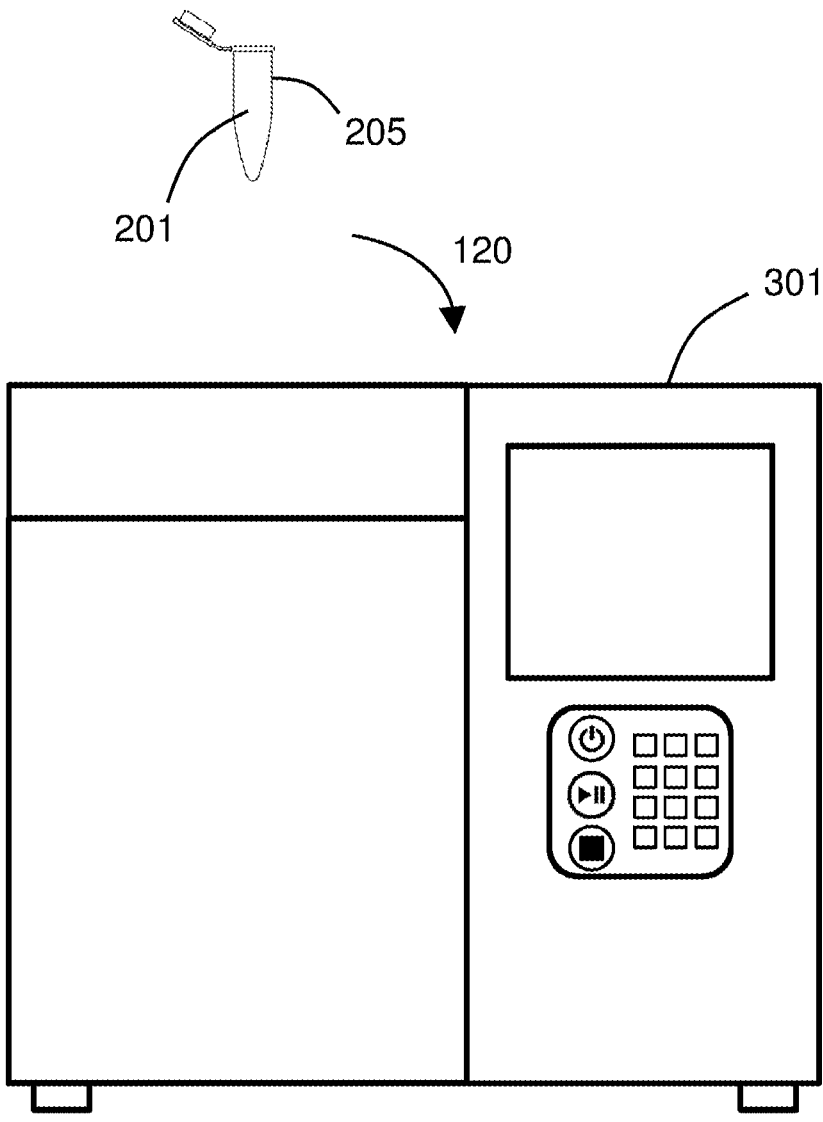
FIG. 3 shows a measurement instrument of the disclosure.

FIG. 3 shows a measurement instrument 301 suitable for making functional measurements of live cells. A sample 201 is obtained 110 (e.g., by blood draw or fine needle aspirate of a solid tumor) and delivered to the instrument 301 in a suitable container 205 such as a microcentrifuge tube sold under the trademark EPPENDORF by Eppendorf, Inc. The sample 201 is introduced 120 onto the measurement instrument 301, which makes a functional measurement of individual living cells in the sample 201.

In certain embodiments, the instrument uses a suspended microchannel resonator (SMR) or serial SMR (sSMR). The SMR may be used to precisely measure biophysical properties, such as mass and mass changes, of a single cell flowing therethrough. Preferably, the mass change is mass accumulation rate (MAR). When used with cancer cells, the changes provide a functional, universal biomarker by which medical professionals (e.g., oncologists) may monitor the progression of a cancer and determine how cancer cells respond to therapies. The SMR comprises an exquisitely sensitive scale that measures small changes in mass of a single cell. When cancer cells respond to cancer drugs, the cells begin the process of dying by changing mass within hours. The SMR detects the minor weight change. The speed and sensitivity allow the SMR to detect a cancer cell's response to a cancer drug while the cell is still living.

Figure 4:
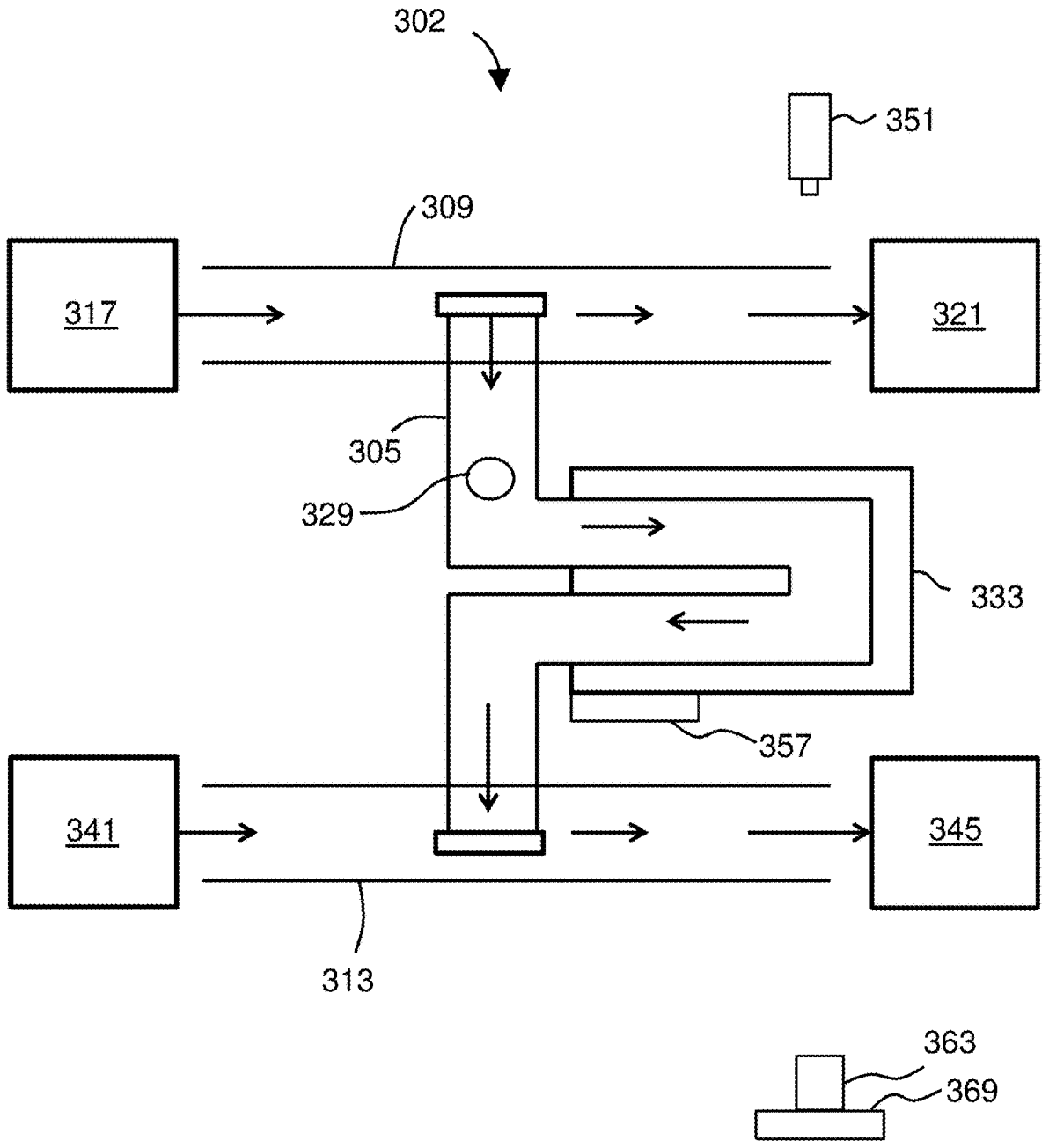
FIG. 4 shows a suspended microchannel resonator (SMR) device.

FIG. 4 shows a suspended microchannel resonator (SMR) device 302. The SMR device 302 includes a microchannel 305 that runs through a cantilever 333, which is suspended between an upper bypass channel 309 and a lower bypass channel 313. Having the two bypass channels allows for decreased flow resistance and accommodates the flow rate through the microchannel 305. Sample eluate 317 flows through the upper bypass channel 309, wherein a portion of the eluate 317 collects in the upper bypass channel waste reservoir 321. A portion of the eluate 317 including at least one live cell 329 flows through the suspended microchannel 305. The flow rate through the suspended microchannel 305 is determined by the pressure difference between its inlet and outlet. Since the flow cross section of the suspended microchannel is about 70 times smaller than that of the bypass channels, the linear flow rate can be much faster in the suspended microchannel than in the bypass channel, even though the pressure difference across the suspended microchannel is small. Therefore, at any given time, it is assumed that the SMR is measuring the eluate that is present at the inlet of the suspended microchannel. The sample includes a live cell or material with cell-like properties.

The cell 329 flows through the suspended microchannel 305. The suspended microchannel 305 extends through a cantilever 333 which sits between a light source 351 and a photodetector 363 connected to a chip 369 such as a field programmable gate array (FPGA). The cantilever is operated on by an actuator, or resonator 357. The resonator 357 may be a piezo-ceramic actuator seated underneath the cantilever 333 for actuation. The cell 329 flows from the upper bypass channel 309 to the inlet of the suspended microchannel 305, through the suspended microchannel 305, and to the outlet of the suspended microchannel 305 toward the lower bypass channel 313. A buffer 341 flows through the lower bypass channel towards a lower bypass channel collection reservoir 345. After the cell 329 is introduced to the lower bypass channel 313, the cell 329 is collected in the lower bypass collection reservoir 345.

Upon flowing the live cells 329 through the SMR device 302, a functional cancer biomarker in the one or more live cells is obtained, the functional cancer biomarker including mass or mass accumulation rate (MAR). MAR measurements characterize heterogeneity in cell growth across cancer cell lines. Individual live cells are able to pass through the SMR, wherein each cell is weighed multiple times over a defined interval. The SMR includes multiple sensors that are fluidically connected, such as in series, and separated by delay channels. Such a design enables a stream of cells to flow through the SMR such that different sensors can concurrently weigh flowing cells in the stream, revealing single-cell MARs. The SMR device 302 provides real-time, high-throughput monitoring of mass change for the cells flowing therethrough. Therefore, the biophysical properties, including mass and/or mass changes (e.g., MAR), of a single cell can be measured. Such data can be stored and used in subsequent analysis steps, as will be described in greater detail herein. Various embodiments of SMR and sSMR instruments and methods of use include those manufactured by Innovative Micro Technology (Santa Barbara, CA) and described in U.S. Pat. Nos. 8,418,535 and 9,132,294, the contents of each of which are hereby incorporated by reference in their entirety.

Precision frequency detection allows the SMR to weigh single living cells, single nanoparticles, and adsorbed protein layers in fluid. Precision is the closeness of agreement between independent test results. When determining SMR resonance frequency optically, the use of an external laser and photodiode are required and cannot be easily arrayed for multiplexed measurements. In embodiments of the present invention, electronic detection of SMR resonance frequency is attained by fabricating piezo-resistive sensors using ion implantation into single crystal silicon resonators. The mass resolution achieved with piezo-resistive detection, such as 3.4 femtogram (fg) in a 1 kHz bandwidth, is comparable to what can be achieved by a conventional optical detector designed to weigh micron-sized particles and cells. Expensive, delicate optical components are not required, thereby providing new uses for the SMR in multiplexed and field deployable applications. For example, piezo-resistive sensors eliminate the need for external components by enabling measurement of deflection through the resistance change of a sensing element integrated onto the cantilever. Microfluidic channels are incorporated inside a cantilever resonator, which significantly reduces viscous damping from fluid and allows buoyant mass to be measured with high resolution.

Upon passing through the instrument 301, single cells remain viable. The cells can be isolated downstream from the instrument 301 and are available to undergo the subsequent assays. As shown, a sample 209 of the one or more live cells having undergone the first assay (i.e., passing through the instrument 301) are collected in a suitable container 213 and are then available to undergo a second assay.

In some embodiments, the instrument 301 comprises an array of SMRs with a fluidic channel passing therethrough.

Figure 5:
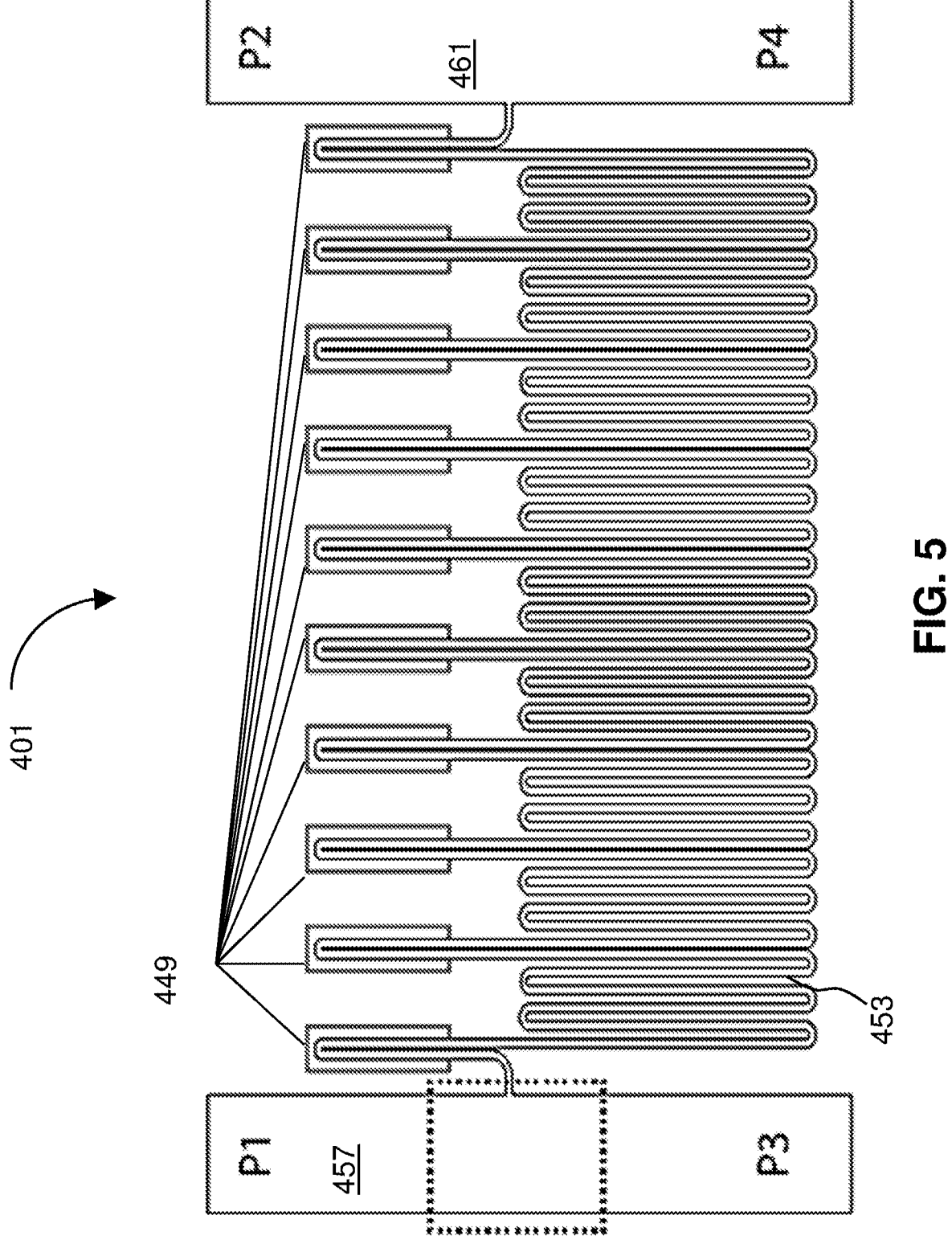
FIG. 5 shows a serial suspended microchannel resonator (sSMR) array.

FIG. 5 shows a serial suspended microchannel resonator (sSMR) array 401, made up of an array of SMRs. An instrument that includes an sSMR array is useful for direct measurement of biophysical properties of single cells flowing therethrough. The sSMR includes a plurality of cantilevers 449 and a plurality of delay channels 453. Cells from the first bypass channel 457 through the cantilevers 449 and delay channels 453 to the second bypass channel 461. Pressure differences in the first bypass channel 457 are indicated by P1 and P2, and pressure differences in the second bypass channel 461 are indicated by P3 and P4.

Instruments 301 of the disclosure make sensitive and precise measurements of mass or change in mass through the use of an sSMR array 401. The instruments use a structure such as a cantilever that contains a fluidic microchannel.

Living cells are flowed through the structure, which is resonated and its frequency of resonation is measured. The frequency at which a structure resonates is dependent on its mass. By measuring the frequency of at which the cantilever resonates, the instrument computes a mass, or change in mass, of a living cell in the fluidic microchannel. Flowing of the cells through such devices allows observation of the functions of those cells, such as whether or not the cells are growing and accumulating mass. Mass accumulation or rate of mass accumulation can be a clinically important property indicating the presence of cancer cells or the efficacy of a therapeutic on cancer cells.

Methods for measuring single-cell growth are based on resonating micromechanical structures. The methods exploit the fact that a micromechanical resonator's natural frequency depends on its mass. Adding cells to a resonator alters the resonator's mass and causes a measurable change in resonant frequency. Suspended microchannel resonators (SMRs) include a sealed microfluidic channel that runs through the interior of a cantilever resonator. The cantilever itself may be housed in an on-chip vacuum cavity, reducing damping and improving frequency (and thus mass) resolution. As a cell in suspension flows through the interior of the cantilever, it transiently changes the resonant frequency of the cantilever in proportion to the buoyant mass of the cell. SMRs weigh single mammalian cells with a resolution of 0.05 pg (0.1% of a cell's buoyant mass) or better. The sSMR array 401 includes an array of SMRs fluidically connected in series and separated by delay channels between each cantilever 349. The delay channels give the cell time to grow as it flows between cantilevers.

Devices may be fabricated as described in Lee, 2011, Suspended microchannel resonators, Lab Chip 11:645 and/ or Burg, 2007, Weighing of biomolecules, Nature 446:1066-1069, both incorporated by reference. Large-channel devices (e.g., useful for PBMC measurements) may have cantilever interior channels of 15 by 20 μm in cross-section, and delay channels 20 by 30 μm in cross-section. Small-channel devices (useful for a wide variety of cell types) may have cantilever channels 3 by 5 μm in cross-section, and delay channels 4 by 15 μm in cross-section. The tips of the cantilevers 449 in the sSMR array 401 may be aligned so that a single line-shaped laser beam can be used for optical-lever readout. The cantilevers may be arrayed such that the shortest (and therefore most sensitive) cantilevers are at the ends of the array. Before use, the sSMR array 401 may be cleaned with piranha (3:1 sulfuric acid to 50% hydrogen peroxide) and the channel walls may be passivated with polyethylene glycol (PEG) grafted onto poly-L-lysine. In some embodiments, a piezo-ceramic actuator seated underneath the device is used for actuation. The instrument 301 may include low-noise photodetector, Wheatstone bridge-based amplifier (for piezo-resistor readout), and high-current piezo-ceramic driver. To avoid the effects of optical interference between signals from different cantilevers (producing harmonics at the difference frequency), the instrument may include a low-coherence-length light source (675 nm super-luminescent diode, 7 nm full-width half maximum spectral width) as an optical lever. After the custom photodetector converts the optical signal to a voltage signal, that signal is fed into an FPGA board, in which an FPGA implements twelve parallel second-order phase-locked loops which each both demodulate and drive a single cantilever. The FPGA may be a Cyclone IV FPGA on a DE2-115 development board operating on a 100 MHz clock with I/O provided via a high-speed AD/DA card operating 14-bit analog-to-digital and digital-to-analog converters at 100 MHz.

To operate all cantilevers 449 in the sSMR array 401, the resonator array transfer function is first measured by sweeping the driving frequency and recording the amplitude and phase of the array response. Parameters for each phase-locked loop (PLL) are calculated such that each cantilever-PLL feedback loop has a 50 or 100 Hz FM-signal bandwidth. The phase-delay for each PLL may be adjusted to maximize the cantilever vibration amplitude. The FM-signal transfer function may be measured for each cantilever-PLL feedback loop to confirm sufficient measurement bandwidth (in case of errors in setting the parameters). That transfer function relates the measured cantilever-PLL oscillation frequency to a cantilever's time-dependent intrinsic resonant frequency. Frequency data for each cantilever are collected at 500 Hz, and may be transmitted from the FPGA to a computer. The device may be placed on a copper heat sink/source connected to a heated water bath, maintained at 37° C. The sample is loaded into the device from vials pressurized under air or air with 5% $CO_2$ through 0.009 inch inner-diameter fluorinated ethylene propylene (FEP) tubing. The pressurized vials may be seated in a temperature-controlled sample-holder throughout the measurement. FEP tubing allows the device to be flushed with piranha solution for cleaning, as piranha will damage most non-fluorinated plastics. To measure a sample of cells, the sSMR array 401 may initially flushed with filtered media, and then the sample may be flushed into one bypass channel. On large-channel devices, between one and two psi may be applied across the entire array, yielding flow rates on the order of 0.5 nL/s (the array's calculated fluidic resistance is approximately $3 \times 10^{\wedge}16$ Pa/(m$^3$/s). For small-channel devices, 4-5 psi may be applied across the array, yielding flow rates around 0.1 nL/s. Every several minutes, a new sample may be flushed into the input bypass channel to prevent particles and cells from settling in the tubing and device. Between experiments, devices may be cleaned with filtered 10% bleach or piranha solution.

For the data analysis, the recorded frequency signals from each cantilever 449 are rescaled by applying a rough correction for the different sensitivities of the cantilevers. Cantilevers differing in only their lengths should have mass sensitivities proportional to their resonant frequencies to the power three-halves. Therefore, each frequency signal is divided by its carrier frequency to the power three-halves such that the signals are of similar magnitude. To detect peaks, the data are filtered with a low pass filter, followed by a nonlinear high pass filter (subtracting the results of a moving quantile filter from the data). Peak locations are found as local minima that occur below a user-defined threshold. After finding the peak locations, the peak heights may be estimated by fitting the surrounding baseline signal (to account for a possible slope in the baseline that was not rejected by the high pass filter), fitting the region surrounding the local minima with a fourth-order polynomial, and finding the maximum difference between the predicted baseline and the local minima polynomial fit. Identifying the peaks corresponding to calibration particles allows one to estimate the mass sensitivity for each cantilever, such that the modal mass for the particles is equal to the expected modal mass.

Peaks at different cantilevers 449 that originate from the same cell are matched up to extract single-cell growth information. The sSMR array 401 can measure live cells.

Certain embodiments include devices with piezo-resistors doped into the base of each cantilever, which are wired in parallel and their combined resistance measured via a Wheatstone bridge-based amplifier. The resulting deflection signal, which consists of the sum of k signals from the cantilever array, goes to an array of k phase-locked loops (PLLs) where each PLL locks to the unique resonant frequency of a single cantilever. Therefore there is a one to one pairing between cantilevers and PLLs. Each PLL determines its assigned cantilever's resonant frequency by demodulating its deflection signal and then generates a sinusoidal drive signal at that frequency. The drive signals from each PLL are then summed and used to drive a single piezo actuator positioned directly underneath the chip, completing the feedback loop. Each PLL is configured such that it will track its cantilever's resonant frequency with a bandwidth of 50 or 100 Hz. After acquiring the frequency signals for each cantilever, the signals are converted to mass units via each cantilever's sensitivity (Hz/pg), which is known precisely.

Various embodiments of SMR and sSMR instruments, as well as methods of use, include those instruments/devices manufactured by Innovative Micro Technology (Santa Barbara, CA) and described in U.S. Pat. Nos. 8,418,535 and 9,132,294, the contents of each of which are hereby incorporated by reference in their entirety.

Figure 6:
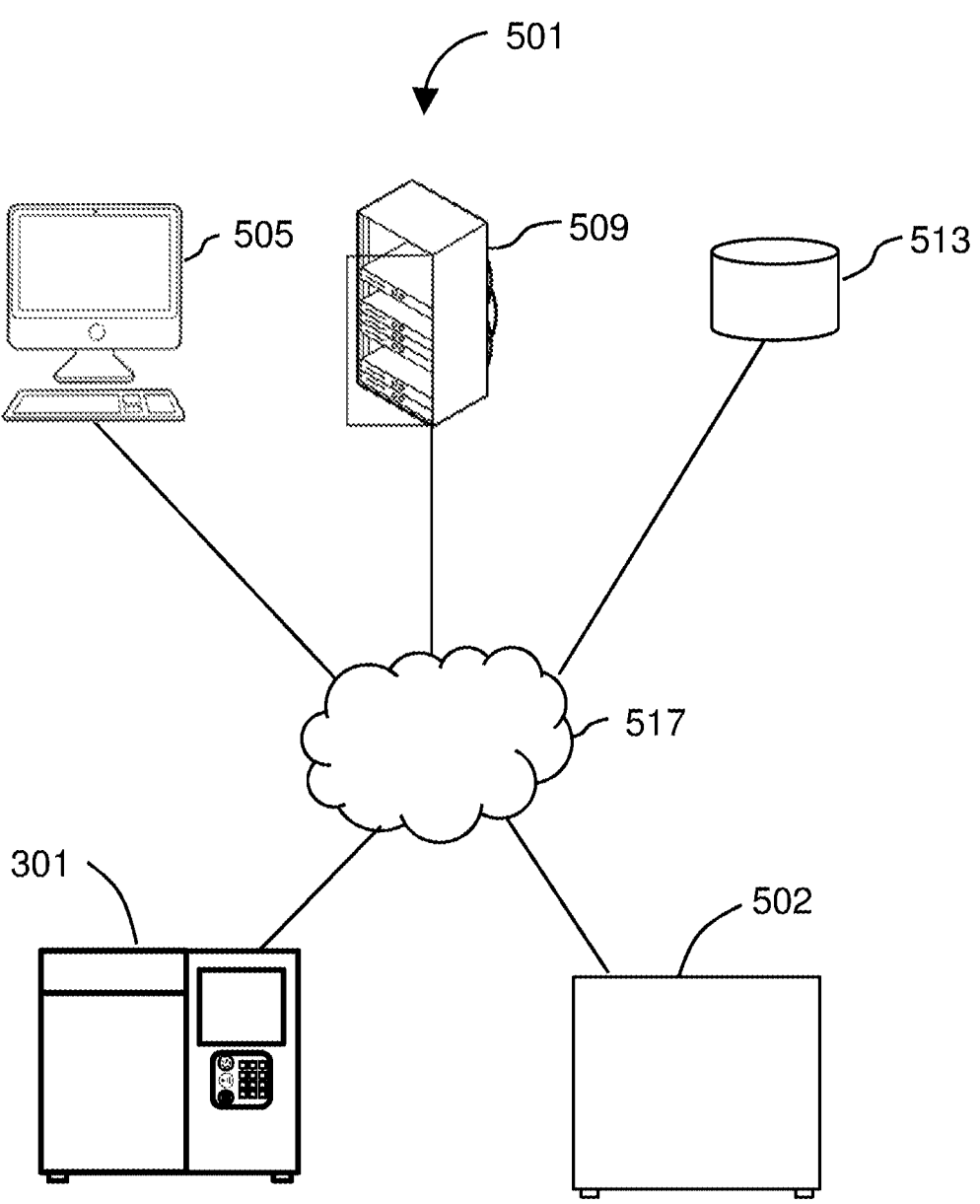
FIG. 6 diagrams a system of the disclosure.

FIG. 6 diagrams a system 501 according to certain embodiments of the disclosure. The system 501 includes an instrument 301 communicatively coupled to a computer 505. The system 501 optionally includes a server 509, storage 513, and one or any number of additional assay instruments 502 (e.g., next-generation sequencing instruments).

Any of the instrument 301, the computer 505, the server 509, the storage 513, and the additional assay instrument 502 that are included preferably exchange data via communication network 517. Where methods of the invention employ client/server architectures, steps of methods of the invention may be performed using the server, which includes one or more of processors and memory, capable of obtaining data, instructions, etc., or providing results via an interface module or providing results as a file. The server may be provided by a single or multiple computer devices, such as the rack-mounted computers sold under the trademark BLADE by Hitachi. In system 501, each computer preferably includes at least one processor coupled to a memory and at least one input/output (I/O) mechanism.

A processor generally includes a chip, such as a single core or multi-core chip, to provide a central processing unit (CPU). A process may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system. Generally, each computer includes a non-transitory memory such as a solid state drive, flash drive, disk drive, hard drive, etc. While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to one or more solid-state memories (e.g., subscriber identity module (SIM) card, secure digital card (SD card), micro SD card, or solid-state drive (SSD)), optical and magnetic media, and/or any other tangible storage medium or media.

A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

The system 501 may be used to perform methods described herein. Instructions for any method step may be stored in memory and a processor may execute those instructions.

Figure 7:
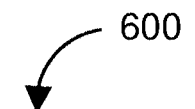
FIG. 7 shows a method according to an embodiment of the invention.
Figure 7:
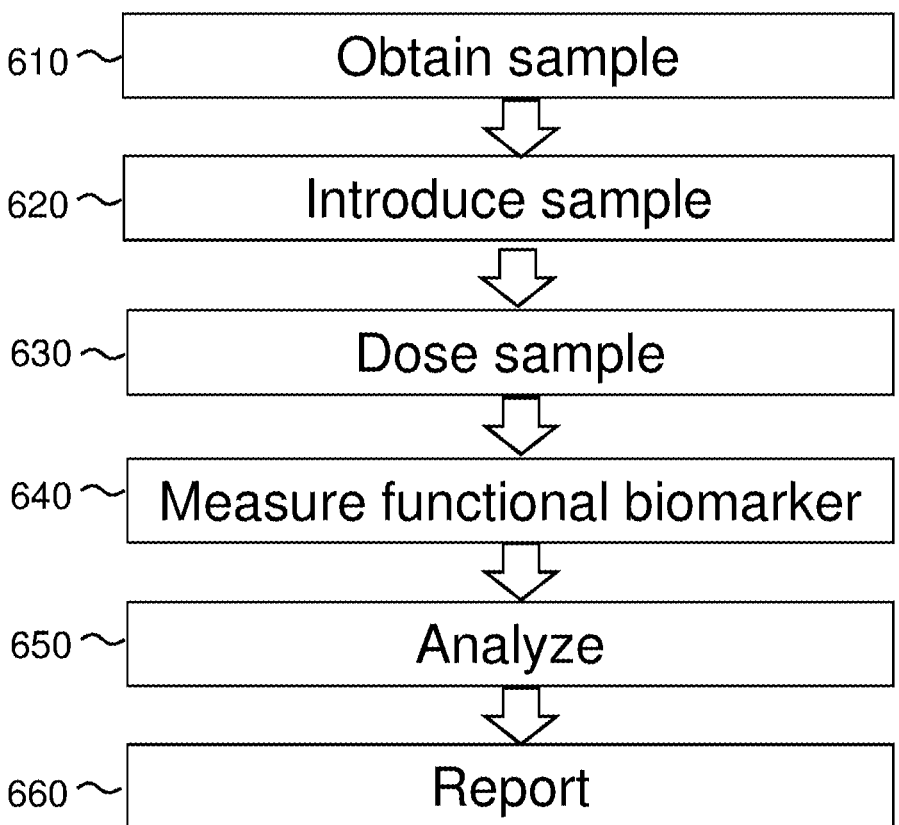

FIG. 7 shows a method 600 according to an embodiment of the invention. The method 600 is directed to rapid functional analysis of cells. The method 600 may comprise a step of obtaining the sample 610 from a subject. The sample may be obtained by any suitable means. Examples of obtaining the sample include fine needle aspiration, liquid biopsy, liquid blood draw, and bone marrow biopsy.

The method 600 comprises introducing the sample 620 by loading a sample onto a microfluidic chip to prepare the sample for functional analysis. The sample comprises at least one living cell. The method further comprises dosing the sample 630. The microfluidic chip comprising the sample may be dosed with a treatment to produce at least one treated living cell. The method further comprises measuring a functional biomarker 640. The functional biomarker may be mass accumulation rate (MAR) of the at least one treated living cell and may be measured while the treated living cell flows through a channel of the microfluidic chip.

In some examples, sample preparation and dosing are performed on a single microfluidic chip. In some examples, sample preparation is performed on a sample preparation chip and dosing is performed on a dosing chip. Sample preparation may comprise positive isolation of the at least one living cell. Sample preparation may comprise negative enrichment of the at least one living cell.

In an example, the dosing chip comprises a dosing cartridge. The dosing cartridge comprises a panel of drugs, such as a panel of drugs specific to cancer, a panel of drugs specific to tissue type, a panel of drugs specific to a stage of a disease, and a panel of drugs specific to a use. The dosing chip may comprise a plurality of reservoirs filled with a plurality of culture media, each culture media comprising a different treatment. In an example, the culture media and treatment is mixed with the at least one living cell at a specified time by controlling a valve on each reservoir. In some examples, the dosing chip comprises temperature control, pH control, and atmosphere control.

In some examples, a measurement chip is used to measure MAR. The measurement chip comprises a serial suspended microchannel resonator (SMR) chip. The SMR chip comprises a serial array of SMR sensors. The measurement chip comprises a plurality of SMR chips in parallel. In an embodiment, measuring MAR comprises flowing a queue of cells in a channel of the SMR back and forth through the SMR sensors. In an embodiment, measuring MAR comprises flowing a queue of cells in a channel of the SMR in a circular fashion through the SMR sensor. The chip comprising a plurality of SMR sensors analyzes multiple conditions concurrently. A plurality of chips, each chip comprising an SMR sensor, may be used to analyze multiple conditions concurrently.

The method 600 may further comprise analyzing the results 650 and producing a report 660. The data obtained from measuring the functional biomarker may be analyzed in step 650. For example, the analysis may specify the mass accumulation rate of the cell and the mass change observed at each sensor. A report may then be provided in step 660. For example, the report may include the analysis results, an indication of whether the dose of the drug administered was effective in preventing mass accumulation, and a recommended treatment based on the analysis.

Methods of the invention include processing fresh patient tissue from steps of introducing the raw sample to the instrument to producing the MAR measurement result. The measurement instrument is any suitable functional biomarker instrument. Preferably, the measurement instrument measures mass accumulation rate or mass change. The measurement instrument includes sample preparation, dosing, and functional measurement components. The functional measurement component may be common to all tissue samples. The sample preparation and dosing components may have differences depending on the tissue, tumor type, disease stage, cell type (cancer vs immune cells), and particular use (clinical, pharma, research etc.). In some examples, the functional measurement component includes at least MAR measurements. In some examples, the live tissue handling techniques developed for the sample preparation and dosing components are applicable to all rapid functional assays that require live cells.

In some embodiments, the invention comprises a dosing chip. In an example, the dosing chip can be in a cartridge form. The cartridge may include a standard panel of drugs specific to a cancer type, tissue type, stage of the disease, or the use. The dosing can be performed automatically in the cartridge in an incubator-like environment and/or instrument. Upon completion of dosing, the cartridge can be presented to the measurement instrument, which may automatically sample cells of different conditions from the cartridge and measure MAR.

In an example, the dosing chip comprises a number of reservoirs filled with culture media with different treatments, or combinations of treatments, pre-stored on the chip. Each reservoir is controlled by a valve to allow a treatment to be mixed with cells and media at a desired time. Since the mechanism of action for each treatment may differ, the dosing chip and/or instrument and/or kit may optimize the treatment initiation time and deliver the cells to the measurement chip at the correct time, or the time where the MAR signal is most significant. Such a chip may have temperature and pH control through an electrical heater and 5% $CO_2$ atmosphere control.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

While the present invention has been described in conjunction with certain embodiments, one of ordinary skill, after reading the foregoing specification, will be able to effect various changes, substitutions of equivalents, and other alterations to the compositions and methods set forth herein.

What is claimed is:

1. A method of rapid functional analysis of cells comprising:

obtaining a sample comprising a live cell from a patient by drawing the sample from a solid tumor by fine needle aspiration and disaggregating the sample to release the live cell;

introducing the live cell into an input reservoir of a measurement instrument, wherein the measurement instrument is a suspended microchannel resonator (SMR);

flowing the live cell through a channel of the measurement instrument; and measuring, within less than about 3 hours after the sample is drawn from the patient, a functional biomarker of the live cell while it flows through the channel, wherein the biomarker is mass or mass accumulation rate (MAR)

wherein the method is performed without an intervening period for culturing the live cell.

2. The method of claim 1, wherein the channel passes through an array of SMRs, in which each successive pair of SMRs is separated by a portion of the channel that provides a delay.

3. The method of claim 1, further comprising washing the live cell from the sample in a nutrient medium, wherein the live cell in the nutrient medium is delivered into the input reservoir in the introducing step.

4. The method of claim 3, wherein the disaggregating step includes exposing a tissue sample or a clump of cells to one or more proteases.

5. The method of claim 3, wherein the nutrient medium comprises a therapeutic.

6. The method of claim 1, wherein the sample comprises no more than 500 cells.

7. The method of claim 1, wherein the live cell leaves the channel after the measuring step in a living state available for a subsequent analysis.

8. The method of claim 1, wherein the live cell is a cancer cell.

9. The method of claim 1, wherein the input reservoir comprises a therapeutic.

10. The method of claim 1, further comprising performing a subsequent assay.

11. The method of claim 10, wherein the subsequent assay is genome sequencing.

12. A method of rapid functional analysis of cells comprising:

obtaining a sample comprising a live cell from a patient by drawing the sample from a solid tumor by fine needle aspiration and disaggregating the sample to release the live cell;

introducing the live cell into an input reservoir of a measurement instrument, wherein the measurement instrument is a suspended microchannel resonator (SMR);

flowing the live cell through a channel of the measurement instrument; and measuring, within less than about 3 hours after the obtaining of the sample, a functional biomarker of the live cell while it flows through the channel, wherein the biomarker is mass or mass accumulation rate (MAR), wherein the method is performed without in vitro culture of the live cell, and wherein the measurement instrument comprises a dosing component that treats the live cell with a therapeutic.

13. The method of claim 12, wherein a duration of dosing is 3 hours to 24 hours.

14. The method of claim 12, further comprising washing the live cell from the sample in a nutrient medium, wherein the live cell in the nutrient medium is delivered into the input reservoir in the introducing step.

15. The method of claim 12, further comprising performing a subsequent assay.

16. The method of claim 15, wherein the subsequent assay is genome sequencing.

* * * * *